United States Patent [19]  [11] 4,362,734
Lesher et al.  [45] Dec. 7, 1982

[54] 2-(SUBSTITUTED-AMINO)-5-(PYRIDINYL-NICOTINONITRILES, AND THEIR CARDIOTONIC USE

[75] Inventors: George Y. Lesher; Chester J. Opalka, Jr., both of Schodack; Donald F. Page, East Greenbush, all of N.Y.

[73] Assignee: Sterling Drug Inc., New York, N.Y.

[21] Appl. No.: 296,300

[22] Filed: Aug. 26, 1981

[51] Int. Cl.$^3$ .................. A61K 31/455; A61K 31/44; C07D 213/85
[52] U.S. Cl. .................................. 424/263; 546/257; 546/258
[58] Field of Search .............................. 546/257–258; 424/263

[56] References Cited

U.S. PATENT DOCUMENTS 4,072,746  2/1978  Lesher et al. ....................... 546/257

FOREIGN PATENT DOCUMENTS 200480  1/1939  Switzerland ........................ 546/293

*Primary Examiner*—Norma S. Milestone
*Attorney, Agent, or Firm*—R. K. Bair; B. Woodrow Wyatt; Paul E. Dupont

[57] ABSTRACT

Shown are cardiotonically active 2-RR'N-5-PY-6-Q-nicotinonitriles where R is methyl or ethyl, R' is hydrogen or methyl, PY is 4- or 3-pyridinyl or 4- or 3-pyridinyl having one or two substituents, and Q is hydrogen or methyl, the latter only when R' is hydrogen, or pharmaceutically acceptable acid-addition salts thereof. Also shown are cardiotonic compositions and a method for increasing cardiac contractility using as active components 2-RR'N-5-PY-6-Q-nicotinonitriles or pharmaceutically acceptable acid-addition salts thereof, where R, R', PY and Q are defined as above. Also shown is the process for preparing said 2-RR'N-5-PY-6-Q-nicotinonitriles by reacting a 2-halo-5-PY-6-Q-nicotinonitrile with an amine of the formula RR'NH.

12 Claims, No Drawings

2-(SUBSTITUTED-AMINO)-5-(PYRIDINYL-NICOTINONITRILES, AND THEIR CARDIOTONIC USE

BACKGROUND OF THE INVENTION (a) Field of the Invention

This invention relates to certain 2-substituted-amino-5-(pyridinyl)nicotinonitriles, their use as cardiotonic agents and to their preparation.

(b) Description of the Prior Art

Lesher and Gruett U.S. Pat. No. 4,264,603, issued Apr. 28, 1981, shows the reaction of a 2-halo-5-(pyridinyl)nicotinonitrile with a hydrazine to produce 5-(pyridinyl)-1H-pyrazolo[3,4-b]pyridin-3-amines, which are useful as cardiotonics.

Lesher and Gruett U.S. Pat. No. 4,264,612, issued Apr. 28, 1981, shows lower-alkyl 2-halo-5-(pyridinyl)-nicotinates and their use as intermediates for preparing 1,2-dihydro-5-(pyridinyl)-3H-pyrazolo[3,4-b]-pyridin-3-ones and their use as cardiotonics, and also shows as intermediates 2-halo-5-(pyridinyl)nicotinoyl halides.

SUMMARY OF THE INVENTION

The invention in a composition of matter aspect resides in 2-RR′N-5-PY-6-Q-nicotinonitrile where R, R′, PY and Q are defined hereinbelow.

A composition aspect of the invention resides in a cardiotonic composition for increasing cardiac contractility comprising a pharmaceutically acceptable carrier and, as the active ingredient thereof, a cardiotonically effective amount of 2-RR′N-5-PY-6-Q-nicotinonitrile or pharmaceutically acceptable acid-addition salt thereof.

In a method aspect the invention resides in a method for increasing cardiac contractility in a patient requiring such treatment which comprises administering a medicament comprising a pharmaceutically acceptable carrier and, as the active component thereof, a cardiotonically effective amount of 2-RR′N-5-PY-6-Q-nicotinonitrile or pharmaceutically acceptable acid-addition salt thereof.

The invention in a process aspect comprises reacting 2-halo-5-PY-6-Q-nicotinonitrile with an amine of the formula RR′NH to produce 2-RR′N-5-PY-6-Q-nicotinonitrile where R, R′, PY and Q are defined hereinbelow.

DETAILED DESCRIPTION INCLUSIVE OF PREFERRED EMBODIMENTS

In a composition of matter aspect the invention resides in 2-RR′N-5-PY-6-Q-nicotinonitrile having the formula I

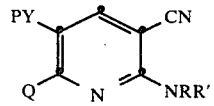

where R is methyl or ethyl, R′ is hydrogen or methyl, PY is 4- or 3-pyridinyl or 4- or 3-pyridinyl having one or two lower-alkyl substituents, and Q is hydrogen or methyl, the latter only when R′ is hydrogen, or pharmaceutically acceptable acid-addition salt thereof. The compounds of formula I are useful as cardiotonic agents, as determined by standard pharmacological evaluation procedures. Preferred embodiments of this aspect of the invention are the compounds where PY is 4-pyridinyl or 3-pyridinyl, R is methyl, R′ is hydrogen or methyl, and Q is hydrogen.

A composition aspect of the invention resides in a cardiotonic composition for increasing cardiac contractility, said composition comprising a pharmaceutically acceptable carrier, and, as the active component thereof, a cardiotonically effective amount of 2-RR′N-5-PY-6-Q-nicotinonitrile of formula I, where Q, R, R′ and PY are each defined as in formula I or pharmaceutically acceptable acid-addition salt thereof. Preferred embodiments are those having as active components the above said preferred embodiments of formula I.

A method aspect of the invention resides in the method for increasing cardiac contractility in a patient requiring such treatment which comprises administering orally or parenterally in a solid or liquid dosage form to such patient said cardiotonic composition comprising a pharmaceutically acceptable carrier and, as the active component thereof, a cardiotonically effective amount of 2-RR′N-5-PY-6-Q-nicotinonitrile of formula I where Q, R, R′ and PY are each defined as in formula I or a pharmaceutically acceptable acid-addition salt thereof.

In a process aspect the invention comprises reacting 2-halo-5-PY-6-Q-nicotinonitrile with an amine of the formula RR′NH to produce 2-RR′N-5-PY-6-Q-nicotinonitrile where halo is chloro or bromo, R is methyl or ethyl, R′ is hydrogen or methyl, PY is 4- or 3-pyridinyl or 4- or 3-pyridinyl having one or two lower-alkyl substituents, and Q is hydrogen or methyl, the latter only when R′ is hydrogen. Preferred embodiments of this process aspect are those wherein PY is 4-pyridinyl or 3-pyridinyl, R is methyl, R′ is hydrogen or methyl, and Q is hydrogen.

Illustrative of PY in formula I where PY is 4- or 3-pyridinyl having 1 or 2 lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The compounds of this invention having formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to use the free base form, the hydrochloride or the methanesulfonate salt; however, appropriate pharmaceutically acceptable salts within the scope of the invention are those derived from other mineral acids such as hydrobromic acid, sulfuric acid, phosphoric acid and sulfamic acid; and organic acids such as acetic acid, citric acid, lactic acid, tartaric acid, ethanesulfonic acid, benzenesulfonic acid, p-toluenesulfonic acid, cyclohexylsulfamic acid, quinic acid, and the like, giving the hydrobromide, sulfate, phosphate, sulfamate, acetate, citrate, lactate, tartrate, ethanesulfonate, benzenesulfonate, cyclohexylsulfamate and quinate, respectively.

The acid-addition salts of said basic compounds (I) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds (I) are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds of formula I were assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same.

The intermediate 2-halo-5-PY-6-Q-nicotinonitriles used in a process aspect of the invention and their preparation are described in said U.S. Pat. No. 4,264,603.

The preparation of 2-RR'N-5-PY-6-Q-nicotinonitriles (I) is carried out by reacting a 2-halo-5-PY-6-Q-nicotinonitrile with RR'NH. The reaction is conveniently run by heating the reactants in a suitable solvent at about 25° C., preferably about 55° C. to 85° C., a preferred procedure being run in refluxing ethanol or tetrahydrofuran or mixture thereof. Alternatively, the reaction can be run by autoclaving the reactants in the absence or preferably in the presence of a suitable solvent, preferably ethanol. Other suitable solvents include dimethylformamide and other lower-alkanols, e.g. isopropyl alcohol, n-propanol.

The following examples will further illustrate the invention without, however, limiting it thereto.

A. 2-RR'N-5-PY-6-Q-NICOTINONITRILES

A-1. 2-Methylamino-5-(4-pyridinyl)nicotinonitrile—To a mixture containing 2-chloro-5-(4-pyridinyl)nicotinonitrile and 400 ml. of absolute ethanol was added 200 ml. of 40% aqeueous methylamine solution and the reaction mixture was refluxed with stirring for 3 hours. The reaction mixture was then filtered and the filtrate chilled. The solid that separated was collected, washed with absolute ethanol and dried in a vacuum oven overnight at 100 mm. and 50° C. to produce 10 g. of 2-methylamino-5-(4-pyridinyl)nicotinonitrile, m.p. 216°–217° C.

Acid-addition salts of 2-methylamino-5-(4-pyridinyl)nicotinonitrile are conveniently prepared by adding to a mixture of 5 g. of 2-methylamino-5-(4-pyridinyl)nicotinonitrile in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively.

Also, the acid-addition salt is conveniently prepared in aqueous solution by adding to water with stirring molar equivalent quantities each of 2-methylamino-5-(4-pyridinyl)nicotinonitrile and the appropriate acid, e.g., lactic acid or hydrochloric acid, to prepare respectively the monolactate or monohydrochloride salt in aqueous solution.

A-2. 2-Dimethylamino-5-(4-pyridinyl)nicotinonitrile—A mixture containing 20 g. of 2-chloro-5-(4-pyridinyl)nicotinonitrile, 200 ml. of 40% aqueous dimethylamine solution and 500 ml. of absolute ethanol was autoclaved at 100° C. for 12 hours. The reaction mixture was heated in vacuo to remove the solvent. The remaining material was recrystallized from absolute ethanol and dried in a vacuum oven at 40° C. for 17 hours to yield 15.8 g. of 2-dimethylamino-5-(4-pyridinyl)nicotinonitrile, m.p. 143°–144° C.

A-3. 6-Methyl-2-methylamino-5-(4-pyridinyl)nicotinonitrile—A mixture containing 20 g. of 2-chloro-6-methyl-5-(4-pyridinyl)nicotinonitrile, 150 ml. of 27% methylamine in ethanol and 300 ml. of tetrahydrofuran was allowed to stand at room temperature for about 3 days. The reaction mixture was heated in vacuo to remove the solvents and excess methylamine and the remaining material was slurried with ammonium hydroxide. The solid was collected, washed with water, recrystallized once from acetone, recrystallized a second time from 1,2-dimethoxyethane using decolorizing charcoal and then recrystallized from acetonitrile and dried to yield 11.6 g. of 6-methyl-2-methylamino-5-(4-pyridinyl)nicotinonitrile, m.p., 161°–163° C.

Following the procedure described in Example A-1 but using in place of 2-chloro-5-(4-pyridinyl)nicotinonitrile and either methylamine or other appropriate amine, RR'NH, molar equivalent quantities of the appropriate 2-halo-5-PY-6-Q-nicotinonitrile and methylamine or other appropriate amine, RR'NH, it is contemplated that the corresponding 2-RR'N-5-PY-6-Q-nicotinonitriles of Examples A-4 through A-15 can be obtained.

A-4. 2-Methylamino-5-(3-pyridinyl)nicotinonitrile.
A-5. 2-Methylamino-5-(2-methyl-3-pyridinyl)nicotinonitrile.
A-6. 2-Ethylamino-5-(5-methyl-3-pyridinyl)nicotinonitrile.
A-7. 2-Methylamino-5-(3-ethyl-4-pyridinyl)nicotinonitrile.
A-8. 2-Dimethylamino-5-(2-methyl-4-pyridinyl)nicotinonitrile.
A-9. 2-Methylamino-5-(2,6-dimethyl-4-pyridinyl)nicotinonitrile.
A-10. 2-Ethylamino-5-(4-pyridinyl)nicotinonitrile.
A-11. 2-Ethylamino-6-methyl-5-(4-pyridinyl)nicotinonitrile.
A-12. 2-(N-Ethyl-N-methylamino)-5-(4-pyridinyl)nicotinonitrile.
A-13. 2-Methylamino-6-methyl-5-(3-pyridinyl)nicotinamide.
A-14. 6-Ethyl-2-methylamino-5-(2-methyl-4-pyridinyl)nicotinonitrile.
A-15. 6-Ethyl-2-methylamino-5-(3-pyridinyl)nicotinonitrile.

The usefulness of the compounds of formula I or salts thereof as cardiotonic agents is demonstrated by their effectiveness in standard pharmacological test procedures, for example, in causing a significant increase in contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by the isolated cat or guinea pig atria and papillary muscle procedure, the compounds of formula I or pharmaceutically-acceptable acid-addition salts thereof at doses of 10, 30 or 100 μg./ml., were found to cause significant increases, that is, greater than 25% or 30% in papillary muscle force and significant increases, that is, greater than 25% or 30%, in right atrial force, while causing a lower percentage increase (about one-third or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, when tested at 10, 30 or 100 mg./ml. in the cat test, the following preferred compound of Example A-1 was found to cause respective increases in papillary muscle force and right atrial force of 63% and 21% at 10 μg/ml., 130% and 45% at 30 μg/ml and 197% and 89% at 100μg/ml. Also, the compound of Example A-2 was found to cause respective increases in cat papillary muscle force and right atrial force of 100% and 31% at 30 μg/ml. and 72% and 32% at 100 μg/ml.; and, the compound of Example A-3 was found to cause respective increases in guinea pig papillary muscle force and right atrial force of 52% and 67% at 100 μg/ml.

The present invention includes within its scope a cardiotonic composition for increasing cardiac contractility, said composition comprising a pharmaceutically-acceptable carrier and, as the active component thereof, the cardiotonic compound of formula I or pharmaceutically acceptable acid-addition salt thereof. The invention also includes within its scope the method for increasing cardiac contractility in a patient requiring such treatment which comprises administering to such patient an effective amount of a cardiotonic compound of formula II or pharmaceutically acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one diluent such as starch, calcium carbonate, surcose or lactose. These compositions can also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspension and emulsions. Examples of organic solvents or suspending media are propylene glycol, polyethylene gylcol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other injectable medium immediately before use.

The percentages of active component in the said compositions and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's rsponse thereto. An effective dosage amount of active component can thus only be determined by the clinician considering all criteria and utilizing the best judgement on the patient's behalf.

We claim:

1. A 2-RR′N-5-PY-6-Q-nicotinonitrile having the formula

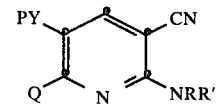

where R is methyl or ethyl, R′ is hydrogen or methyl, PY is 4- or 3-pyridinyl or 4- or 3-pyridinyl having one or two lower-alkyl substituents, and Q is hydrogen or methyl, the latter only when R′ is hydrogen, or pharmaceutically acceptable acid-addition salt thereof.

2. A compound according to claim 1 where PY is 4-pyridinyl or 3-pyridinyl, R is methyl, R′ is hydrogen or methyl and Q is hydrogen.

3. 2-Methylamino-5-(4-pyridinyl)nicotinonitrile or pharmaceutically acceptable acid-addition salt thereof.

4. 2-Dimethylamino-5-(4-pyridinyl)nicotinonitrile or pharmaceutically acceptable acid-addition salt thereof.

5. A cardiotonic composition for increasing cardiac contractility, said composition comprising a pharmaceutically acceptable inert carrier and, as the active component thereof, a cardiotonically effective amount of 2-RR′N-5PY-6-Q-nicotinonitrile or pharmaceutically acceptable acid-addition salt thereof, where R is methyl or ethyl, R′ is hydrogen or methyl, Q is hydrogen or methyl, the latter only when R′ is hydrogen, and PY is 4- or 3-pyridinyl or 4- or 3-pyridinyl having one or two lower-alkyl substituents.

6. A composition according to claim 5, where PY is 4-pyridinyl or 3-pyridinyl, R is methyl, R′ is hydrogen or methyl and Q is hydrogen.

7. A composition according claim 5 where the active component is 2-methylamino-5-(4-pyridinyl)nicotinonitrile or pharmaceutically acceptable acid-addition salt thereof.

8. A composition according to claim 5 where the active component is 2-dimethylamino-5-(4-pyridinyl)-nicotinonitrile or pharmaceutically acceptable acid-addition salt thereof.

9. The method for increasing cardiac contractility in a patient requiring such treatment which comprises administering orally or parenterally in a solid or liquid dosage form to such patient said cardiotonic composition of claim 5.

10. The method for increasing cardiac contractility in a patient requiring such treatment which comprises administering orally or parenterally in a solid or liquid dosage form to such patient said cardiotonic composition of claim 6.

11. The method for increasing cardiac contractility in a patient requiring such treatment which comprises administering orally or parenterally in a solid or liquid dosage form to such patient said cardiotonic composition of claim 7.

12. The method for increasing cardiac contractility in a patient requiring such treatment which comprises administering orally or parenterally in a solid or liquid dosage form to such patient said cardiotonic composition of claim 8.

* * * * *

UNITED STATES PATENT AND TRADEMARK OFFICE
CERTIFICATE OF CORRECTION

PATENT NO. : 4,362,734
DATED : December 5, 1982
INVENTOR(S) : G. Y. Lesher et al.

It is certified that error appears in the above–identified patent and that said Letters Patent are hereby corrected as shown below:

Column 3, line 37, insert -- to 100°C. -- between "25°C." and ",".

Column 6, line 27, "rsponse" should read -- response --.

Claim 5, line 5, "5PY" should read -- 5-PY --.

Signed and Sealed this

Fifteenth Day of May 1984

[SEAL]

Attest:

GERALD J. MOSSINGHOFF

Attesting Officer

Commissioner of Patents and Trademarks